United States Patent [19]

Matthews

[11] 3,932,557

[45] Jan. 13, 1976

[54] REACTIVE HYDROPHILIC EPOXY CONTAINING POLYMER

[75] Inventor: Joseph S. Matthews, O'Hara Township, Pa.

[73] Assignee: Gulf Research & Development Company, Pittsburgh, Pa.

[22] Filed: Dec. 19, 1972

[21] Appl. No.: 316,451

[52] U.S. Cl............ 260/837 R; 260/8; 260/47 UA; 260/47 EP; 260/63; 260/79.7; 260/85.5 R; 260/85.5 B; 260/86.1 E; 260/824 EP; 260/827; 260/836

[51] Int. Cl.$^2$............ C08L 63/00; C08F 28/00; C08F 220/42; C08L 89/00

[58] Field of Search ..... 260/85.5 R, 85.5 B, 47 UA, 260/86.1, 88.3 A, 837, 79.7, 63, 47 EP

[56] References Cited
UNITED STATES PATENTS

| 2,524,432 | 10/1950 | Dorough | 260/85.5 B |
|---|---|---|---|
| 2,570,601 | 10/1951 | Schmerling | 260/85.5 B |
| 2,580,901 | 1/1952 | Erickson et al. | 260/85.5 B |
| 2,650,151 | 8/1953 | Ham | 260/85.5 B |
| 2,824,851 | 2/1958 | Hall | 260/837 R |
| 3,294,769 | 12/1966 | Hicks | 260/85.5 R |
| 3,301,743 | 1/1967 | Fekete et al. | 260/837 R |
| 3,317,465 | 5/1967 | Doyle et al. | 260/836 |
| 3,373,075 | 3/1968 | Fekete et al. | 260/837 R |
| 3,377,406 | 4/1968 | Newey et al. | 260/837 R |
| 3,408,422 | 10/1968 | May | 260/837 R |
| 3,420,914 | 1/1969 | May | 260/837 R |
| 3,432,478 | 3/1969 | May | 260/837 R |
| 3,679,447 | 7/1972 | Aronoff et al. | 260/47 UA |
| 3,697,218 | 10/1972 | Nakajima et al. | 260/85.5 B |

Primary Examiner—Joseph L. Schofer
Assistant Examiner—Herbert J. Lilling

ABSTRACT

A hydrophilic, epoxy containing polymer. The polymer is made by the free radical polymerization of a substituted epoxy monomer containing terminal unsaturation and at least one 1,2-epoxy group with an olefin monomer such as acrylonitrile to form a polymer having free epoxy groups which are available for reaction with other substances. Enzymes are immobilized by reaction with the polymer.

6 Claims, No Drawings

REACTIVE HYDROPHILIC EPOXY CONTAINING POLYMER

The invention relates to a hydrophilic, epoxy containing polymer having free, reactive epoxy groups and to a method for preparing the polymer.

The novel epoxy-containing polymer of my invention is prepared by the reaction of an epoxy monomer having at least one 1,2-epoxy group and one terminal unsaturation per molecule when the epoxy molecule is a single chemical species or per average molecule when the epoxy monomer is a mixture of chemical species as a result of its method of preparation. Suitable available epoxy monomers include glycidyl acrylate, glycidyl methacrylate, allyl glycidyl ether, and the like. Other epoxy monomers which are useful for preparing the epoxy containing polymer include those which are prepared by the reaction of an epoxy resin with a difunctional olefin to form the epoxy monomer as defined. The epoxy monomer is then copolymerized with a substituted olefin monomer by free radical polymerization to form a hydrophilic polymer which contains reactive epoxy groups.

Many enzymes can be separated from their natural environment in a living organism and recovered for catalytic use such as, for example, in an industrial process or in a suitable analytical application. Since enzymes are water soluble, some enzymes function in their natural environment in solution, however, most enzymes function within the living organism in association with a membrane. When an enzyme is removed from the organism and is used as a catalyst in an aqueous solution, it tends to become denatured because of reduced stability in the foreign environment. Furthermore, it is difficult to recover active enzyme catalyst for reuse from the product solution containing the enzyme and impurities. It has been proposed to artificially insolubilize enzymes to overcome these disadvantages by chemically or physically attaching the enzyme to a water-insoluble substrate or support to form a synthetically immobilized enzyme analogous to the membrane-enzyme relationship in nature.

The solid and water-insoluble, hydrophilic, epoxy containing polymer of my invention can synthetically immobilize and support enzymes by chemically uniting with an enzyme or mixture of enzymes. Both the stability and the activity during storage and use of the resulting immobilized enzyme are thereby substantially enhanced by the hydrophilic environment provided by the epoxy containing polymer. Not only does the enzyme, immobilized by the epoxy containing polymer, retain its natural activity to a substantial degree, but it can also be repeatedly reused in a batch process or used over extended periods of time in a continuous process with substantial retention of its activity.

In the immobilized enzyme the enzyme is chemically bound or coupled to the epoxy containing polymer through one or more epoxy groups of the support or carrier. This coupling reaction takes place with a suitable functional group in the enzyme molecule. Since an epoxy group can react with many different functional groups, the epoxy containing polymer carrier is reactive with and can immobilize any enzyme which is capable of being immobilized. Thus, the present epoxy containing polymer can advantageously immobilize a large number and variety of enzymes for catalytic utility or can be reacted with other substances, as desired.

The expressions epoxy resin and polyepoxide are used interchangeably to refer to the broad class of initial epoxide containing reactants which are used in the reaction of the difunctional olefin with the epoxy resin to form the epoxy monomer. The epoxy resin can be a single compound or a mixture of compounds containing the alpha-epoxy group and can be monomeric or polymeric. Each epoxy group can be located terminally, internally, or on a cyclic structure that is capable of being used in preparing a thermoset material. The expressions are used with reference to the thermoplastic or uncured state and do not refer to a thermoset or cured material. When the epoxy resin is a single compound, it must contain at least two epoxy groups per molecule. However, with epoxy resins or polyepoxides in which a variety of molecular species are present, the number of epoxy groups will vary from molecular species to molecular species such that the average number of epoxy groups per molecule is specified.

This average number of epoxy groups per molecule is also designated the epoxy equivalent value. When a mixture of compounds is involved, the epoxy equivalent value must be greater than one and preferably at least about two but will generally not be a whole integer. The epoxy equivalent value is obtained by dividing the average molecular weight of the epoxy resin by its epoxide equivalent weight (grams of epoxy resin containing one gram equivalent of epoxide). The epoxy resin can be aliphatic, cycloaliphatic, aromatic, heterocyclic, mixtures of these, saturated or unsaturated, and can include non-interfering groups such as halogen, alkoxy, ester and the like.

This broad class of epoxy resins which is useful in forming the epoxy containing polymer is exemplified by reference to several of the better known types. Glycidyl group epoxy resins are an important type of epoxy resin. This includes the glycidyl ethers, the glycidyl esters, the glycidyl amines, the thioglycidyl resins, the silicon glycidyl resins and the like. The glycidyl ethers include the glycidyl ethers of mononuclear polyhydric phenols, polynuclear polyhydric phenols and the aliphatic polyols. They may be single compounds or more commonly are a mixture of compounds, some of which are polymeric in nature. Illustrative of glycidyl ethers are the di or polyglycidyl ethers of ethylene glycol; trimethylene glycol; glycerol; diglycerol; erythritol; mannitol; sorbitol; polyallyl alcohol; dihydroxymethylcyclohexene; polyepichlorohydrin; butanediol; hydrogenated bisphenol A; 1,3-bis(3-hydroxypropyl)tetramethyldisiloxane; 2,5-bis(hydroxymethyl)tetrahydrofuran; 1,4:3,6-dianhydro-D-sorbitol; 2-butynediol; and the like.

The glycidyl ethers of polyhydric phenols include the glycidyl ethers of resorcinol; hydroquinone; catechol; pyrogallol; phloroglucinol; their methyl derivatives; and the like as well as the glycidyl ethers of polynuclear phenols such as 2,2-bis(4-hydroxyphenyl)propane; bis(4-hydroxyphenyl)methane; 2,2-bis(4-hydroxyphenyl)isobutane; 2,2-bis(2-hydroxynaphthyl)pentane; 1,5-dihydroxynaphthalene; bisphenol A; 4,4'-dihydroxybiphenyl; 2,3',4-tri(epoxytripropoxy)diphenyl; dihydroxyfluoroanthrene; dihydroxydinaphthylmethane, and the like, and glycidyl ethers of the novolac resins such as bisphenol F.

The epoxy resins also include epoxidized polyolefins generally based on naturally occurring polyolefins such as epoxidized soybean oil, epoxidized cotton seed oil, epoxidized castor oil, epoxidized linseed oil, epoxidized menhaden oil, epoxidized lard oil and the like, but also including epoxidized butadiene, epoxidized polybutadiene, and the like. They also include epoxy resins obtained from chloroacetyl compounds such as 4,4-bis(1,2-epoxyethyl)phenyl ether; 1,3,5(1,2-epoxyethyl)benzene; 1,5(1,2-epoxyethyl)naphthalene; 4,4'-bis(1,2-epoxyethyl)biphenyl; and the like.

Additional useful epoxy resins are diglycidyl isophthalate; diglycidyl phthalate; O-glycidyl phenyl glycidyl ether; 2,6-(2,3-epoxypropyl)phenylglycidyl ether; triglycidyl p-aminophenol; diglycidyl ether of bisphenol-hexafluoroacetone; diglycidyl ether of 2,2-bis(4-hydroxyphenyl)nonadecane; diglycidyl phenyl ether; triglycidyl 4,4-bis(4-hydroxyphenyl)-pentanoic acid; diglycidyl ether of tetrachlorobisphenol A; triglycidyl ether of trihydroxybiphenyl; tetraglycidoxy biphenyl; tetraglycidyl ether of bisresorcinol F; tetraglycidyl ether of resorcinol ketone; diglycidyl ether of bisphenol PA, triglycidoxy-1,1,3-triphenylpropane; and the like. Also included are tetraglycidoxy tetraphenyl ethane; 1,3-bis[3-(2,3-epoxypropoxy)-propyl]tetramethyldisiloxane; diglycidyl ether of polypropylene glycol; polyallyl glydicyl ether; triglycidyl ester of linoleic trimer acid; epoxidized cyclic silane; diglycidyl ether of chlorendic diol; diglycidyl ether of dioxanediol; diglycidyl ether of endomethylene cyclohexanediol; diglycidyl ester of linoleic dimer acid; and the like.

Further examples of epoxy resins are 2,2-bis[4-(2,3-epoxypropyl)cyclohexyl]propane; 2,2-(4-[3-chloro-2-(2,3-epoxypropoxy)propoxyl]cyclohexyl)propane; vinylcyclohexenedioxide; limonene dioxide; 2,2-bis(3,4-epoxycyclohexyl)propane; diglycidyl ether; bis(2,3-epoxycyclopentyl)ether; dicyclopentadiene dioxide; 1,2-epoxy-6-(2,3-epoxypropoxy)hexahydro-4,7-methanoindane; p-epoxycyclopentylphenyl glycidyl ether; epoxydicyclopentyl glycidyl ether; O-epoxycyclopentylphenyl -epoxycyclopentylphenyl glycidyl ether; bisepoxydicyclopentyl ether of ethylene glycol; 3,4-epoxycyclohexylmethyl-(3,4-epoxy)cyclohexane carboxylate; 3,4-epoxy-6-methylcyclohexylmethyl-4-epoxy-6-methylcyclohexane carboxylate; dicycloaliphatic diether diepoxy; bis(3,4-epoxy-6-methylcyclohexylmethyl)adipate; and the like. Further information on these epoxy resins and additional examples of useful epoxy resins are discussed and/or referred to in HANDBOOK OF EPOXY RESINS by H. Lee and K. Neville, McGraw-Hill Book Co., 1967.

The difunctional olefin can be defined by the following structural formula

where $R_1$ is hydrogen or methyl and $R_2$ is carboxyl; hydroxymethyl; formyl; chlorocarbonyl; carbamyl; aminomethyl; mercaptocarbonyl; mercaptomethyl;

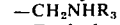

where $R_3$ is lower alkyl, hydroxyphenyl or lower alkyl substituted hydroxyphenyl; or lower alkyl or phenyl substituted hydroxyphenyl. Lower alkyl refers to alkyl groups having one to four carbon atoms. Suitable difunctional olefins include acrylic acid, methacrylic acid, allyl alcohol, acrolein, methacrolein, acrylyl chloride, acrylamide, allylamine, thioacrylic acid, allyl mercaptan, vinyl phenol, and the like.

The difunctional olefin reacts through the functional group other than the unsaturated group with an epoxy group in the polyepoxide in order to form the epoxy monomer. This reaction is illustrated with acrylic acid and a diepoxy resin:

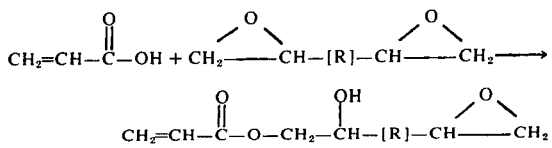

where R merely represents the non-epoxy portion of the polyepoxide. Since the preparation of an epoxy containing polymer is the objective, it is preferable that the amount of the difunctional olefin relative to the epoxy resin be less than the amount that would react with every epoxy group in order that unreacted epoxy groups are available for subsequent reaction after the polymer is formed. Therefore, the ratio of mol equivalents of epoxy groups to difunctional olefin should preferably be greater than one. It is preferred that this ratio be at least about two to one in the reaction mixture used to make the epoxy monomer. This is simply accomplished by using an equimolar mixture of epoxy resin and difunctional olefin in which the epoxy resin has an epoxy equivalent value of at least about two.

The epoxy monomer can be conveniently prepared under conditions for reflux at a temperature between about 100° and about 150° C. and atmospheric pressure. A suitable solvent for the difunctional olefin and the epoxy resin, which is non-reactive in the reaction environment, is selected having a boiling point at the desired reflux temperature. Temperatures below about 100° C. can be used at a lowered reaction rate and temperatures above about 150° C. can be used provided that the materials are stable at the high temperature. The solvent can be toluene, xylene, chlorobenzene, tetrachloroethylene, bromoform, n-butylacetate, acetonitrile, dioxane, dimethyl ether and the like, which are illustrative of the classes of compounds that can serve as a solvent in the reaction.

A catalyst is preferably used for the desired reaction between the epoxy resin and the difunctional olefin. Suitable catalysts for this reaction are the alkyl and aromatic tertiary amines including trimethylamine, triethylamine, tripropylamine, tributylamine, benzyldimethylamine, benzyldiethylamine, pyridine, 2-picoline, 4-picoline, 2,6-lutidine, and the like. The reflux is carried out until the reaction is substantially complete. The epoxy monomer is next copolymerized with the substituted olefinic monomer.

The substituted olefinic monomer copolymerizes with the epoxy monomer by free radical polymerization at the olefinic double bonds in each material. The substituted olefinic monomers are suitable for copolymerization with the epoxy monomer to produce hydrophilic epoxy containing polymers without substantial reaction with the epoxy groups in the epoxy monomer. The preferred substituted olefinic monomers can be defined by the structural formula

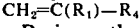

where $R_1$ is methyl or hydrogen and $R_4$ is cyano, lower carboalkoxy having one to four carbon alkoxy, and the like and include acrylonitrile, methacrylonitrile, methyl acrylate, methyl methacrylate, and the like. Since the substituted olefinic monomer introduces the hydrophilic property into the polymer, the relative amount of this monomer can be varied to adjust this property. Suitable hydrophilic epoxy containing polymers are made when the epoxy monomer comprises about five to about 30 mol percent of the comonomer mixture.

Suitable free radical initiation can be used such as ionizing radiation, ultraviolet radiation and the like, but preferably chemical free radical initiators are used. The chemical free radical initiators together with accelerators or activators, if needed, are selected according to common practice by correlating the desired temperature of polymerization with the activation temperature of the initiators. Suitable chemical free radical initiators include benzoyl peroxide, lauroyl peroxide, methyl ethyl ketone peroxide, di(2-methylpentanoyl)peroxide, p-chlorobenzoyl peroxide, cyclohexanone peroxide, bis(1-hydroxycyclohexyl)peroxide, hydroxyheptyl peroxide, and the like, dicyclohexyl peroxydicarbonate, dibenzyl peroxydicarbonate, azobisisobutyronitrile, and the like. The polymerization reaction is carried out using a suitable, non-reactive solvent for the monomers generally at a temperature between about 80° C. and about 200° C. Suitable solvents include the solvents specified for the preparation of the epoxy monomer. The same solvent can be conveniently used in each reaction. Following polymerization the polymer is dried of the solvent and formed into a fine powder.

The polymer product is a solid hydrophilic polymer which contains a substantial number of epoxy groups at the surface of the particles available for reaction with other compositions. In order to bind an enzyme to the water-insoluble epoxy containing polymer, the polymer is dispersed in a water solution of an enzyme. Generally the weight of the enzyme in solution is no greater than about one percent of the weight of the polymer support. In the upper end of this range, the enzyme is used in excess over that amount which can be bound. However, the enzyme does not need to be used in excess since only a sufficient amount of enzyme is used in the immobilization reaction to produce a product of useful activity. During the immobilization reaction, the enzyme comes into reactive contact with the polymer aided by the hydrophilic nature of the polymer. The binding reaction occurs through one or more of the large number of epoxy groups available for reaction on the surface of the polymer particles and through one or more epoxy reactive groups in the enzyme. Epoxy reactive groups are listed in Appendix 5–1 of the Lee and Neville book.

This binding reaction is preferably carried out at a low temperature, such as 0° to 10° C., to avoid undue denaturation of the enzyme and with gentle agitation to insure good contact of the enzyme with the polymer. This enzyme immobilization reaction is carried out for a long enough time to bind a useful amount of the enzyme on the polymer generally from about one to about eight hours. The enzyme-polymer product is then filtered and washed with buffered aqueous solution to remove non-bound enzyme, and is left moist to maintain the activity of enzyme. The immobilized enzyme is used as a catalyst in contact with an aqueous solution of the substance undergoing conversion. It possesses a substantial portion of its natural activity and it can be repeatedly recovered for reuse and can be used for long periods of time without substantial loss of activity.

The following examples are set out to illustrate the invention and to provide a better understanding of its details and advantages. An International Unit (I.U.) is defined as the amount of enzyme which converts one micromol of substrate per minute.

EXAMPLE 1

A 27 gram portion of methacrylonitrile and 250 ml. of benzene were placed in a 500 ml. resin kettle equipped with mechanical stirrer, condenser, nitrogen inlet and heating mantle. The conventional anti-oxidant-polymerization inhibitor had first been removed from the methacrylonitrile by passing it through a column of silica gel. To this solution were added 14.2 grams of glycidyl methacrylate and one gram of azobisisobutyronitrile. The solution was heated at reflux with stirring for 18 hours. The cloudy solution was then slowly poured into two liters of rapidly stirred hexane to produce a flocculent white solid. The solid product was filtered, washed with hexane, dried under vacuum and then ground to a powder. This epoxy containing product was determined to have an epoxy equivalent value of about 900 and was obtained in 32 percent (13 grams) yield based on total reactants.

A one gram sample of the polymer was placed in a 30 ml. screw cap bottle along with 10.0 ml. of a glucose oxidase solution having an activity of 100 I.U. The bottle and contents were shaken overnight at a temperature of about 0° C. A colorimetric analysis of the polymer and solution demonstrated that the polymer had immobilized 0.037 mg. of glucose oxidase per gram of polymer and was determined to have an activity of 10 I.U.

EXAMPLE 2

A 27 gram (0.05 mol) portion of Epon 834 (a diglycidyl ether of bisphenol A having an epoxy equivalent value of 280 obtained from Shell Chemical Company) dissolved in 100 ml. of toluene, 8.2 grams (0.1 mol) of methacrylic acid and 1.0 ml. of triethylamine were placed in the resin kettle described in Example 1. The reaction mixture was refluxed with stirring under a nitrogen atmosphere as one ml. samples of the reaction mixture were periodically sampled and titrated with 0.1 N sodium hydroxide to analyze for methacrylic acid. When analysis indicated that about 95 percent of the methacrylic acid had been consumed, 50 ml. of toluene were removed by distillation.

This was followed by the addition of 200 ml. of benzene and 27 grams (0.4 mol) of methacrylonitrile (purified as described in Example 1) and one gram of azobisisobutyronitrile. The reaction mixture was stirred under reflux for five hours during which time the polymer product came out of solution. The polymer product was filtered, washed with benzene, ground and dried under vacuum yielding 61 percent based on total reactants (38 grams) of a fluffy, white powdered polymer product having an epoxy equivalent value of 3,817.

A 0.5 gram portion of this polymer was shaken for four hours with 5.0 ml. of glucose oxidase solution having an activity of 105 I.U. Colorimetric analysis revealed that the polymer had immobilized 0.117 mg. of glucose oxidase per gram of polymer. This immobilized product had an activity of 27 I.U.

EXAMPLE 3

The procedure of Example 2 was repeated except that 13.5 grams (0.2 mol) of methacrylonitrile was used in the polymerization. A fluffy, white polymer product was produced in 80 percent yield (39 grams) based on the total reactants. Its epoxy equivalent value was 4,950. A 0.5 gram portion of this polymer was shaken with 5.0 ml. of a glucose oxidase solution having an activity of 113 I.U. After four hours the polymer and solution were analyzed, colorimetrically establishing that the polymer had immobilized 0.210 mg. of glucose oxidase per gram of polymer. The activity of the immobilized enzyme was 27 I.U.

EXAMPLE 4

A 35 gram (0.088 mol) portion of D.E.R. 736 resin (a Dow Chemical Company diglycidyl ether of propylene glycol having an epoxy equivalent value of 200), 7.2 grams (0.1 mol) of acrylic acid, one ml. of triethylamine and 100 ml. of toluene were placed in a three-neck flask. The mixture was refluxed with agitation under a nitrogen atmosphere until the free acid was consumed. The solution was transferred to a 250 ml. volumetric flask and sufficient benzene was added to bring the solution to 250 ml. The 42.2 grams of epoxy monomer were found to have an epoxy equivalent value of 505.

A 74 ml. portion (0.025 mol) of the epoxy monomer solution, 47.5 grams (0.475 mol) of methylmethacrylate, 200 ml. of benzene and one gram of azobisisobutyronitrile were placed in a 500 ml. resin kettle and stirred under reflux and a nitrogen atmosphere for five hours. The product was poured into two liters of rapidly stirred hexane and the resulting solid was powdered and dried under vacuum. The resulting fine white powder weighed 52.8 grams, a yield of 88 percent based on the total reactants, and had an epoxy equivalent value of 3,340.

One gram of this epoxy containing polymer was shaken overnight at 0° C. with 10 ml. of a glucose oxidase solution having an activity of 150 I.U. The polymer and solution were analyzed colorimetrically showing that the polymer had taken up 0.015 mg. glucose oxidase with an activity of 26 I.U.

It is to be understood that the above disclosure is by way of specific example and that numerous modifications and variations are available to those of ordinary skill in the art without departing from the true spirit and scope of my invention.

I claim:

1. A solid, hydrophilic epoxy containing polymer which is the reaction product of the free radical polymerization at the olefinic double bonds without substantial epoxy reaction of (a) about 70 to 95 mol percent of a substituted olefin monomer having the formula $$CH_2=C(R_1)-R_4$$

in which $R_1$ is hydrogen or methyl and $R_4$ is cyano or lower carboalkoxy with (b) about five to about 30 mol percent of an epoxy monomer containing terminal unsaturation and one 1,2-epoxy group in which the epoxy monomer is the reaction product of (1) a diepoxide with (2) a difunctional olefin at a mol ratio of diepoxide to difunctional olefin of about one to one, said difunctional olefin having an unsaturated group and a second functional group and defined by the structural formula $$CH_2=C(R_1)-R_2$$

in which $R_1$ is hydrogen or methyl and $R_2$ is carboxyl; hydroxymethyl; formyl; chlorocarbonyl, carbamyl; aminomethyl; mercaptocarbonyl; mercaptomethyl; lower alkyl or phenyl substituted hydroxyphenyl; or $$-CH_2NHR_3$$

where $R_3$ is lower alkyl, hydroxyphenyl or lower alkyl substituted hydroxyphenyl, and said diepoxide having reacted with the difunctional olefin through an epoxy group of said diepoxide with the said second functional group of said difunctional olefin.

2. An epoxy containing polymer in accordance with claim 1 in which the substituted olefin monomer is acrylonitrile or methacrylonitrile.

3. An epoxy containing polymer in accordance with claim 1 in which the diepoxide is a diglycidyl ether of bisphenol A.

4. An epoxy containing polymer in accordance with claim 1 in which $R_2$ is carboxyl, hydroxymethyl, formyl, chlorocarbonyl, carbamyl or aminomethyl.

5. An epoxy containing polymer in accordance with claim 1 in which $R_2$ is carboxyl.

6. The solid, hydrophilic epoxy containing polymer which is the reaction product of the free radical polymerization of about 70 to about 95 mol percent of acrylonitrile, methacrylonitrile, methyl methacrylate or methyl acrylate with about five to 30 mol percent of an epoxy containing monomer having terminal unsaturation which is the reaction product of about one mol of a diglycidyl ether of bisphenol A per mol of acrylic acid or methacrylic acid, said acrylic acid or methacrylic acid having reacted through the acid group with an epoxy group in the diglycidyl ether of bisphenol A.

* * * * *